United States Patent
Chernyakhovsky et al.

(10) Patent No.: US 10,327,668 B2
(45) Date of Patent: Jun. 25, 2019

(54) SPIROMETER SYSTEM AND METHOD FOR DETERMINING LUNG FUNCTIONAL RESIDUAL CAPACITY (FRC) WITH A NON-OCCLUDING SHUTTER

(71) Applicants: TEL HASHOMER MEDICAL RESEARCH, INFRASTRUCTURE & SERVICES LTD., Ramat-Gan (IL); Leonid Chernyakhovsky, Ashdod (IL); Hanan Itzkovitch, Tel-Aviv Yafo (IL)

(72) Inventors: Leonid Chernyakhovsky, Ashdod (IL); Hanan Itzkovitch, Tel-Aviv Yafo (IL); Mark Gaides, Ashdod (IL)

( * ) Notice: Subject to any disclaimer, the term of this patent is extended or adjusted under 35 U.S.C. 154(b) by 514 days.

(21) Appl. No.: 14/913,009

(22) PCT Filed: Aug. 13, 2014

(86) PCT No.: PCT/IL2014/050728
§ 371 (c)(1),
(2) Date: Feb. 19, 2016

(87) PCT Pub. No.: WO2015/025316
PCT Pub. Date: Feb. 26, 2015

(65) Prior Publication Data
US 2016/0198980 A1    Jul. 14, 2016

Related U.S. Application Data

(60) Provisional application No. 61/867,489, filed on Aug. 19, 2013.

(51) Int. Cl.
*A61B 5/09* (2006.01)
*A61B 5/087* (2006.01)
(Continued)

(52) U.S. Cl.
CPC ............ *A61B 5/087* (2013.01); *A61B 5/0876* (2013.01); *A61B 5/09* (2013.01); *A61B 5/091* (2013.01);
(Continued)

(58) Field of Classification Search
USPC ........................................................ 600/538
See application file for complete search history.

(56) References Cited

U.S. PATENT DOCUMENTS

| 4,220,161 A | 9/1980 | Berlin et al. |
|---|---|---|
| 5,233,998 A | 8/1993 | Chowienczyk et al. |

(Continued)

FOREIGN PATENT DOCUMENTS

| CN | 101208044 | 6/2008 |
|---|---|---|
| EP | 0419113 | 3/1991 |

(Continued)

OTHER PUBLICATIONS

International Search Report, dated Dec. 15, 2014 in corresponding application No. PCT/I2014/050728.

*Primary Examiner* — Tiffany Weston
*Assistant Examiner* — Tho Q Tran
(74) *Attorney, Agent, or Firm* — Browdy and Neimark, PLLC

(57) ABSTRACT

The present invention relates to a device, system and a method for determining lung volume and parameters, and in particular, to such a spirometer device, system and method in which a non-occluding shutter is utilized allowing for continuous airflow through the flow tube.

13 Claims, 8 Drawing Sheets

(51) Int. Cl.
*A61B 5/091* (2006.01)
*A61B 5/097* (2006.01)
*G01F 17/00* (2006.01)
*G01F 22/02* (2006.01)
*A61B 5/00* (2006.01)

(52) U.S. Cl.
CPC ............... *A61B 5/097* (2013.01); *A61B 5/72* (2013.01); *G01F 17/00* (2013.01); *G01F 22/02* (2013.01); *A61B 2562/0247* (2013.01)

(56) References Cited

U.S. PATENT DOCUMENTS

| | | |
|---|---|---|
| 5,261,397 A | 11/1993 | Grunstein |
| 5,584,300 A | 12/1996 | Gaides |
| 5,857,459 A | 1/1999 | Snow et al. |
| 5,868,681 A * | 2/1999 | Schiller .................. A61B 5/085 600/533 |
| 6,066,101 A | 5/2000 | Johnson et al. |
| 6,113,550 A | 9/2000 | Wilson |
| 6,183,423 B1 | 2/2001 | Gaumond et al. |
| 2007/0144520 A1 | 6/2007 | Heinonen |
| 2010/0242622 A1 * | 9/2010 | Weckstrom ............. A61B 5/087 73/861.52 |
| 2010/0286548 A1 | 11/2010 | Lazar et al. |
| 2011/0201958 A1 * | 8/2011 | Lazar .................... A61B 5/091 600/538 |
| 2011/0282228 A1 | 11/2011 | Shiner et al. |
| 2013/0190640 A1 | 7/2013 | Adam et al. |
| 2013/0213131 A1 * | 8/2013 | Speldrich ................. G01F 5/00 73/202.5 |

FOREIGN PATENT DOCUMENTS

| | | | |
|---|---|---|---|
| WO | 2006/130922 | 12/2006 | |
| WO | WO2009/013755 A2 * | 1/2009 | ............... A61B 5/03 |

* cited by examiner

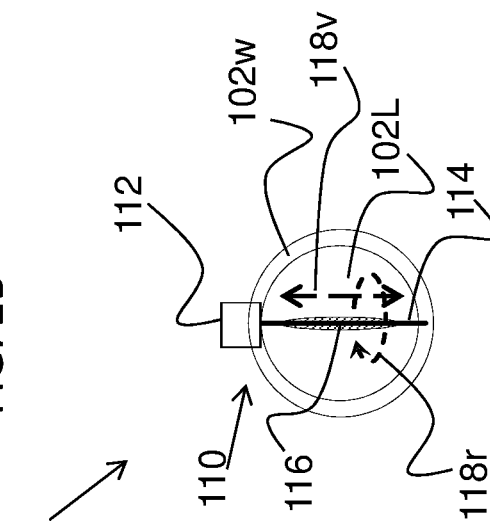
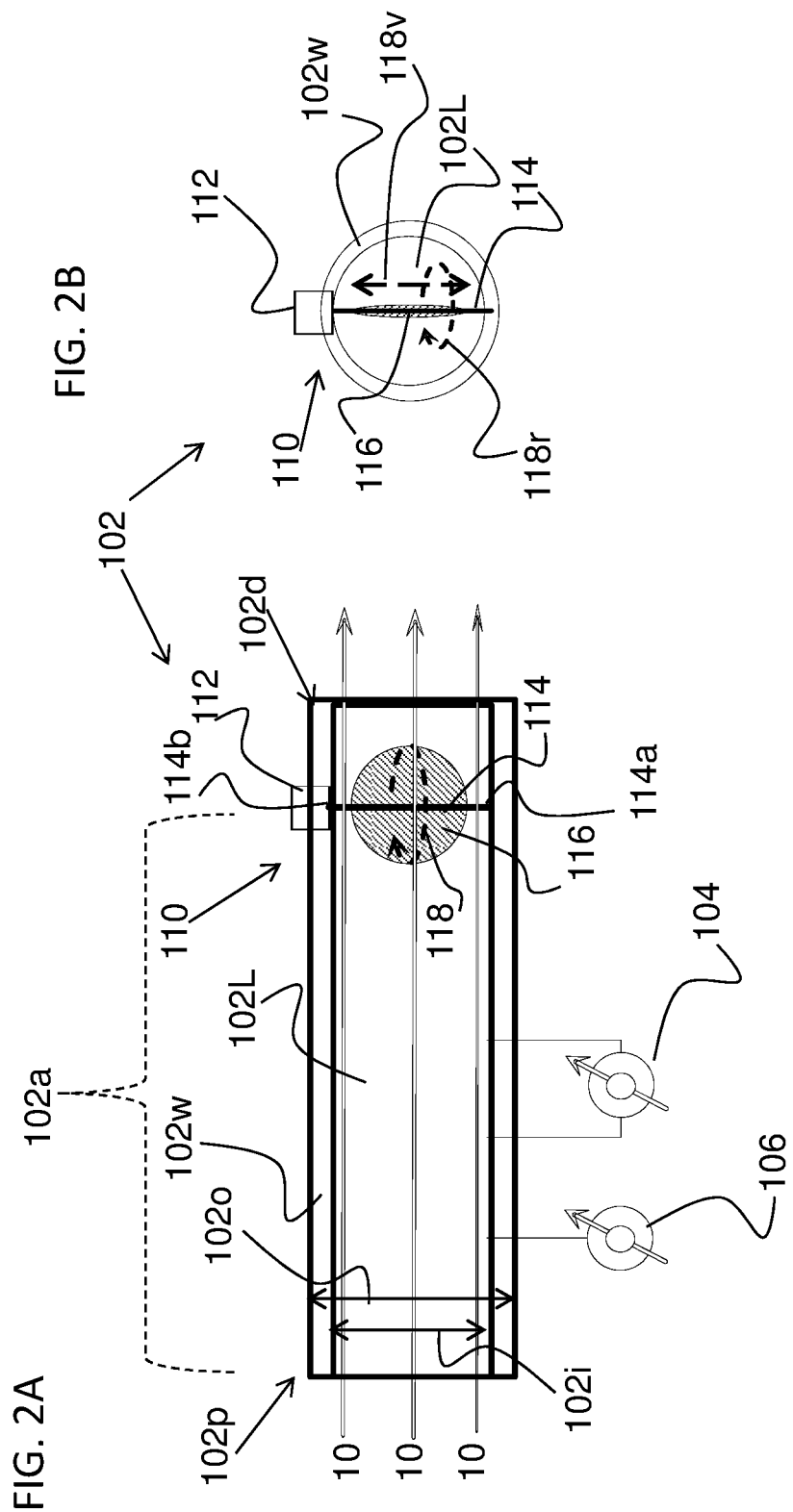

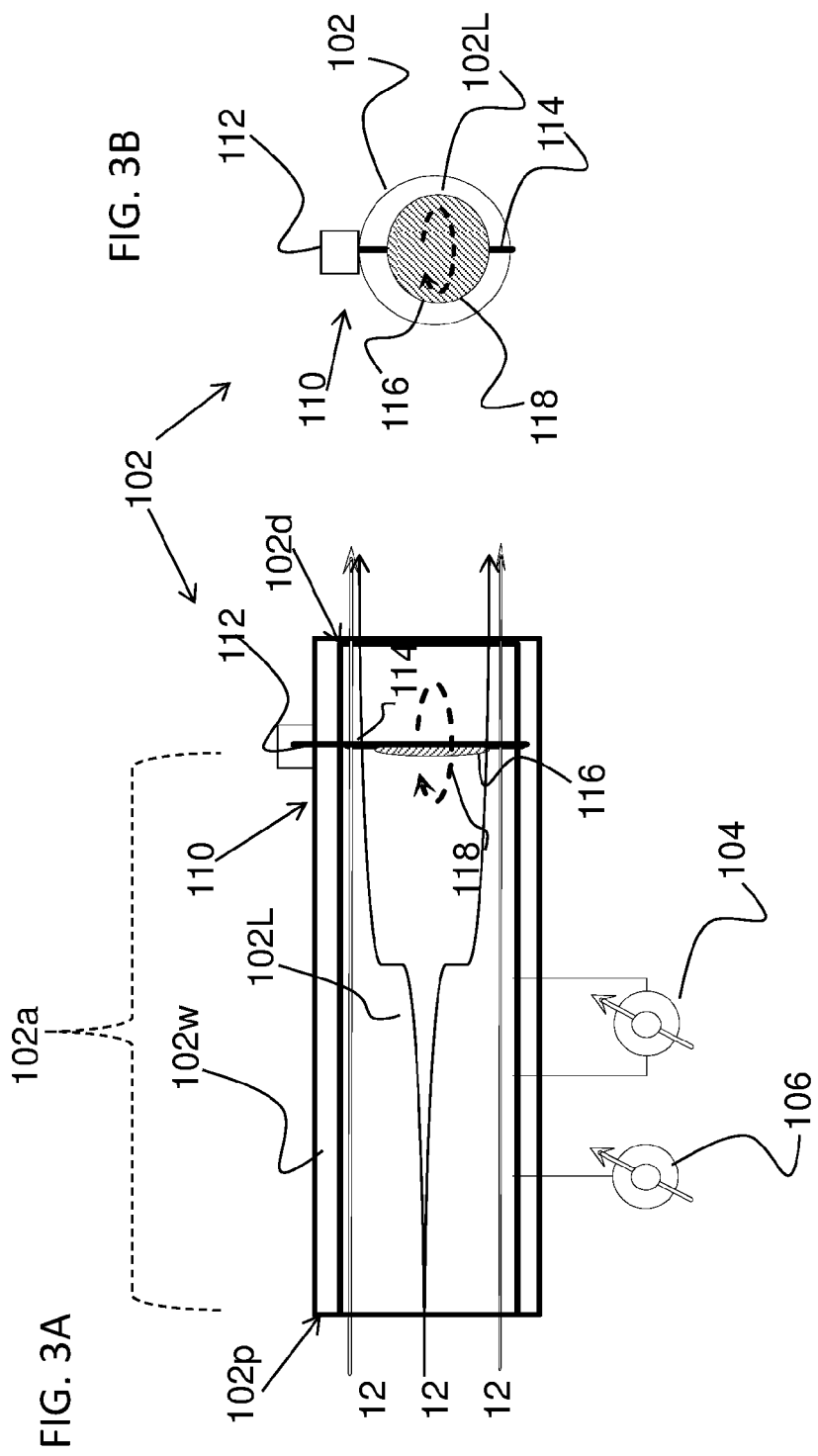

SPIROMETER SYSTEM AND METHOD FOR DETERMINING LUNG FUNCTIONAL RESIDUAL CAPACITY (FRC) WITH A NON-OCCLUDING SHUTTER

FIELD OF THE INVENTION

The present invention relates to a device, system and a method for determining lung volume and parameters, and in particular, to such a spirometer device, system and method in which a non-occluding shutter is utilized allowing for continuous airflow through the flow-tube during measurement.

BACKGROUND OF THE INVENTION

For a variety of diagnostic and related reasons, it is important to be able to accurately determine lung volume. Such measurements are crucial in evaluating lung damage as a result of disease or trauma. The measurements are also important in analyzing the extent to which blood is accommodated in the lungs during breathing, for example under stress conditions.

Accurately determining an individual's lung volume is a key parameter in pulmonary physiology and diagnosis but one that is not easily measured, as it involves various parameters and cannot be readily measured based the volume of air exhaled. The difficulty in measuring lung volume measurements stems from the fact that the lungs do not fully collapse. Lung physiology and the mechanical properties of the lungs and chest wall, including the ribs, leave a significant amount of air in the aerated portions of the lungs, after exhaling fully.

Although it is relatively straightforward to measure the volume of air which is exhaled, at the end of complete exhalation, this is not indicative of true lung volume, as a significant amount of air is always left in the lungs. This is due to the fact that the lungs do not collapse completely, complicating lung volume measurements.

The gas left in the lungs at the end of a complete exhalation is termed the Residual Volume (RV) which may be significantly increased in disease states. The total volume of gas in the lungs at the end of a maximal inspiration is termed the Total Lung Capacity (TLC) which includes the RV plus the maximum amount of gas which can be inhaled or exhaled, which is termed the Vital Capacity (VC).

As previously indicated, during normal breathing the subject does not empty the lungs down to RV nor inflate them to TLC. The amount of gas in the lungs at the end of a normal breath is termed the Functional Residual Capacity (FRC), which is distinct from a complete exhalation. A further measurement is Total Gas Volume (TGV) of the lungs in a patient.

Various techniques have been proposed for measuring the various lung air volumes. At least two of these techniques are in common use including gas dilution and plethysmography technique utilizing a device called a body box, The gas dilution technique makes use of a spirometer which contains a certain known concentration of a gas not normally found in the lungs, such as helium. After steady state is achieved the gas is analyzed chemically and the determined concentration of the helium is used to calculate the patient's FRC.

However the gas dilution technique requires the use of certain expensive and difficult to handle gases, such as helium and xenon. Furthermore, the technique requires the use of a gas analyzer. Finally, it is not normally possible to use the technique to measure lung capacity under stress since the measurement typically takes from 3 to 7 minutes which is ordinarily longer than the time of the stress.

During plethysmography a patient is placed in a body box which is hermetically sealed and utilized to measure the TGV. While in the sealed body box the patient breathes through a breathing tube. The airflow through the breathing tube is blocked at certain intervals. By blocking the airflow while in a sealed and controlled environment allows the measurement of relating the changes in pressure in the chamber to calculate the patient's TGV utilizing Boyle's law.

However, the plethysmography or body box technique requires large and expensive body box. Furthermore the device is cumbersome and is not applicable for ambulatory use, or home use requiring appropriate clinical environment and conditions. The body box does not allow for performing the measurement under stress conditions since the body box is confining and since stress would lead to a warming of the air in the body box, thereby reducing the accuracy of the measurements. Finally, the plethysmography technique requires the patient to simulate normal breathing but with a blocked breathing tube which is difficult for some people to accomplish, especially old people and young children, that further reduces the accuracy of the technique The body box further requires patient active cooperation and therefore cannot be performed on immobile individuals or individuals confined to a bed or patients in a vegetative state or comatose patients.

Body plethysmograph devices for determination of TGV are disclosed, for example, in U.S. Pat. No. 6,113,550 to Wilson, and have been known and used since at least 1955. Other devices, which include the use of impedance belts have been disclosed as well, for example, in U.S. Pat. No. 5,857,459. In both types of devices, the plethysmograph chamber or the impedance belts are designed so that the volume in the lungs can be calculated directly, so as to provide reliable measurement parameters for calculation of TGV. As indicated above these methods for measuring TGV are all less than optimal, requiring a sealed chamber in which the subject sits, or external belts which have been shown not to provide reliable results and which may be bulky, expensive and inconvenient to operate, and require full cooperation of the subject during the measurement maneuvers to obtain meaningful results Recent developments for example as described in US Patent Publication No. US 2011/0282228 describe a desk top device that offers an alternative to the body box method for determining lung volumes utilizing a method known as partial volume method. The partial volume method utilizes short interruptions of airflow through the flow tube in order to determine the lung volume. Such desk top devices, while they are smaller and more compact than the body box, are still cumbersome and do not provide an ambulatory solution.

Other small scale devices that provide an alternative to the body box are described in U.S. Pat. No. 6,183,423 to Gaumond et al; U.S. Pat. No. 5,233,998 to Chowienczyk et al. Both devices utilize controlled short interruptions of airflow where airflow through the flow tube is occluded, in order to allow for measurements of lung volumes using inferences from Boyle's law.

SUMMARY OF THE INVENTION

The present invention overcomes the deficiencies of the background by providing a device, system and method utilizing a spirometer flow tube characterized in that the spirometer's shutter is provided in the form of a non-occluding leaf shutter. Preferably the non-occluding leaf shutter provides for deflecting air within the flow tube such that it does not occlude airflow through the flow tube that in turn allows a patient to maintain normal breathing physiology during use.

In maintaining normal breathing physiology during use the spirometer flow tube according to optional embodiments of the present invention provides for use in ambulatory conditions, home use conditions, clinical conditions and for patients in varying degrees of consciousness and/or ability to cooperate with physicians during use.

Optionally the non-occluding leaf may assume at least two profile configurations within the flow tube relative to the radial cross section of the flow tube; a first configuration in the form of a low profile configuration relative to the radial cross section of the flow tube, and a second configuration in the form of an expanded non-occluding profile configuration.

Optionally and preferably the non-occluding leaf shutter provides for maintaining airflow through the flow tube therein allowing the patient to maintain normal breathing physiology during.

Optionally the non-occluding leaf shutter may assume a radial cross-sectional surface area that is up to about 50% of the radial cross-sectional area of the flow tube. Optionally the leaf shutter may assume a radial cross-sectional surface area that is from about 1% of the radial cross-sectional area of the flow tube.

Optionally the non-occluding leaf shutter may be provided in any shape or geometric configuration.

Optionally the non-occluding leaf shutter may be sized relative to the sensitivity of a pressure sensor or flow-meter device associated with the flow tube.

Optionally and preferably the spirometer according to the present invention provides a method for determine lung Functional Residual Capacity ('FRC').

Optionally and preferably the spirometer according to the present invention may be used as part of a computerized system provides for determine lung Functional Residual Capacity ('FRC').

Within the context of this application the term non-occluding shutter and deflecting leaf, leaf, non-occluding leaf, deflecting members may be used interchangeably to refer to a member disposed within the flow tube that may assume at least two or more profiles about the radial cross section of the flow tube, a low profile and an expanded profile. Both profiles are configured to allow maintain normal breathing physiology and do not occlude the flow tube. However, the expanded profile is configured to have a larger surface area relative to the flow tube's cross sectional area. Both low profile and expanded profile configuration are adapted to have a cross sectional area that is up to about 50%, and optionally from about 1% of the radial cross-sectional area of the flow tube of the radial cross-sectional area of the flow tube Unless otherwise defined the various embodiment of the present invention may be provided to an end user in a plurality of formats/platforms, and may be outputted to at least one of a computer readable memory, computer readable media, a computer display device, a printout, a computer on a network or a user.

Unless otherwise defined, all technical and scientific terms used herein have the same meaning as commonly understood by one of ordinary skill in the art to which this invention belongs.

The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Within the context of this application the term processor, processing module, microprocessor or the like may be used to refer to any device featuring a data processor and/or the like computational properties and/or the ability to execute one or more instructions for example including but not limited to a computer, computer network, PC (personal computer), a server, a minicomputer, a cellular telephone, a smart phone, a PDA (personal data assistant), mobile communication device, mobile processing device, any two or more of such devices in communication with each other, and/or any computer in communication with any other computer, may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2A-B show schematic illustrations of an exemplary spirometer with a shutter leaf in the low profile configuration according to an optional embodiment of the present invention; FIG. 2A shows a side view, FIG. 2B shows a face on view;

FIG. 3A-B show schematic illustrations of an exemplary spirometer with a shutter leaf in the expanded configuration, according to an optional embodiment of the present invention; FIG. 3A depicting a side view, FIG. 3B depicting a face on view;

DESCRIPTION OF THE PREFERRED EMBODIMENTS

The principles and operation of the present invention may be better understood with reference to the drawings and the accompanying description.

The following figure reference labels are used throughout the description to refer to similarly functioning components are used throughout the specification hereinbelow.

Figure 1:
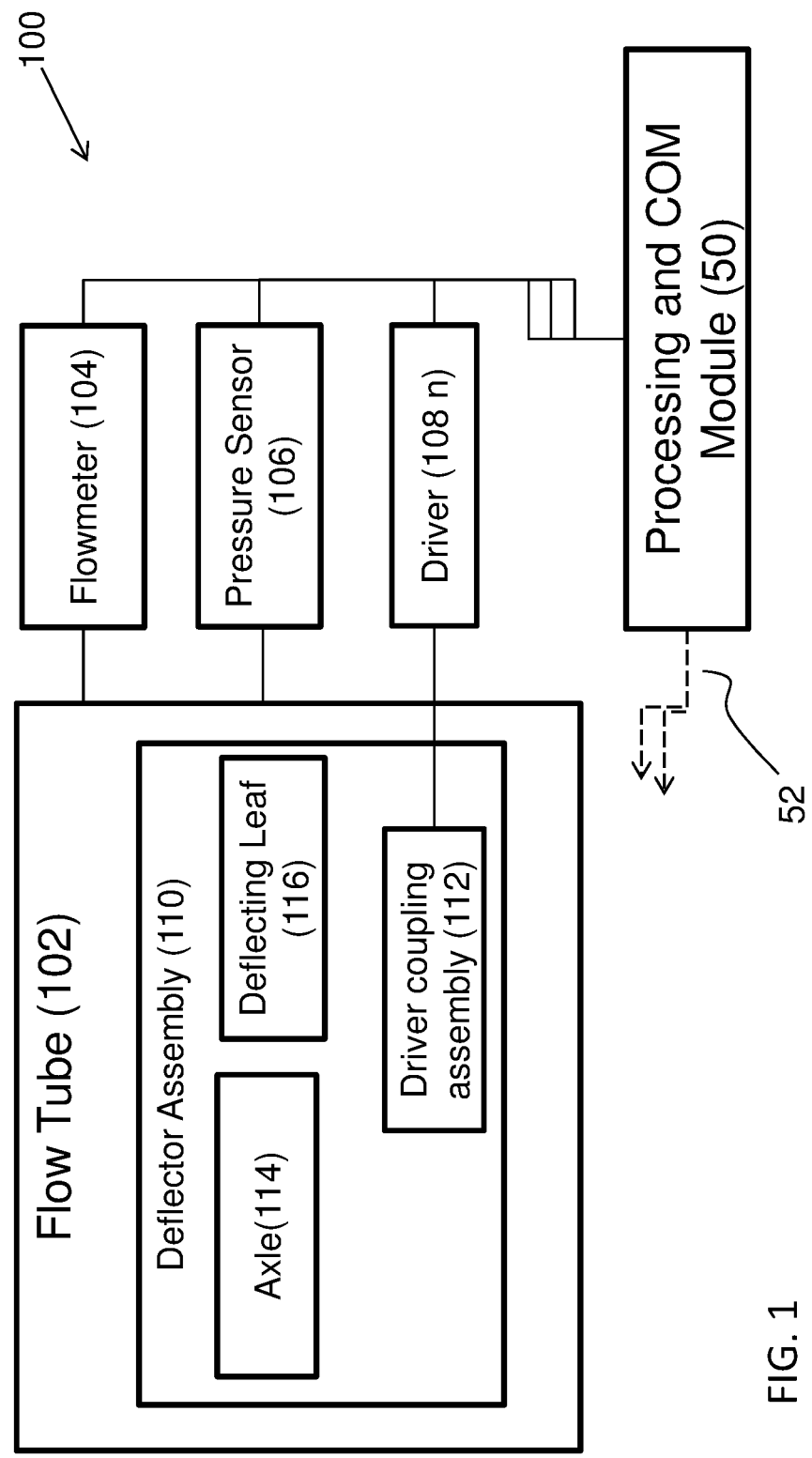
FIG. 1 is a schematic block diagram of an exemplary device and system according to the present invention.

10 Open air flow
12 deflected air flow;
50 Data processing and communication module;
52 communication channels;
100 Flow Tube system
102 Flow Tube;
102d Flow Tube distal end;
102p Flow Tube proximal end;
102L flow tube lumen;
102w flow tube wall;
104 Flow meter;
106 Pressure Sensor;
108 driver;
110 Flow Deflector Apparatus
112 axle adaptor/coupling assembly;
114 Axle;
114a axle first end;
114b axle second end;
114d axle distance;
116 deflector leaf/shutter;
116d Leaf diameter;
118r deflector rotational (x-y) axis;
118v deflector vertical (z) axis;
120 deflector driver;

Referring now to the drawings, FIG. 1 is a schematic block diagram of an exemplary flow tube spirometer 102 forming an integral part of system 100 according to the present invention for.

System 100 comprises flow tube 102, where the flow tube is functionally associated with at least two sensors 104, 106, provided in the form of a pressure sensor 106 and a flow meter sensor 104, deflector assembly 110, a driver 108 for controlling the deflector assembly 110, and a processing and communication module 50. Optionally the flow meter may be provided in optional form as is known in the art. For example including but not limited to pneumotachograph, a Doppler flow meter, ultrasonic flow meter, filaments flow meter, the like or any combination thereof.

Optionally processing and communication module 50 may be provided in the form of a computer, server, computer network, a mobile communication device, smartphone, processor, processing module, microprocessor, any device featuring a data processor and/or the like computational and communication, the like.

Optionally module 50 may be linked and/or in wirelessly communication channels 52 with other processing centers, servers, computers or the like. Optionally module 50 may be linked electronically with a health care provider server, health management organization server, call center, emergency care service provider, physician, nurse, trained individual, the like or any combination thereof.

Optionally communication channels 52 may be provided in optional forms for example including but not limited to wired, wireless, cellular, near field, contactless, optical, radio frequency, infrared the like or any combination thereof.

Most preferably module 50 is provided for processing and/or communicating data gathered by sensors and actuators, for example flow sensor 104, pressure sensor 106, driver 108 that are associated with flow tube 102.

Most preferably module 50 provides for determining and/or inferring the lung FRC based on the data gathered and provided by flow tube 102.

Optionally module 50 may be in communication with flow sensor 104, pressure sensor 106, and driver 108. Optionally and preferably module 50 may be utilized to activate and/or control the sensors 104,106 and actuators 108 associated with flow tube 102. For example module 50 may be utilized to control the frequency and activity of driver 108.

Optionally driver 108 may be realized as an integrated member of module 50.

Driver 108 may also be referred to as an actuator and/or motor that is provided to actuate and/or drive deflector assembly 110. Optionally driver 108 may be provided in the form of a motor, piezoelectric actuator, servo motor, or the like.

Preferably driver 108 is provided for actuating and/or driving deflector assembly 110 via a driver coupling assembly 112 that is provided to couple axle 114 with driver 108. Optionally actuating axle 114 may be provided by driver assembly 108 directly or indirectly via coupling assembly 112. Optionally coupling assembly 112 may be provided in the form of an adaptor. Optionally coupling assembly 112 may be provided in the form of a converter, modulator or the like for example in the form of a gear box or the like provided to convert the actuation of motor 108 to movement by axle 114 that in turn depicts the movement of deflector leaf 116 within the lumen of flow tube 102. Optionally axle 114 may optionally provide for maneuvering deflector leaf about its axis about a planar rotational axis 118r about or a vertical axis.

Most preferably deflecting apparatus 110 is disposed within the lumen of a flow tube 102. Flow tube 102 may be provided as a substantially cylindrical tube 102. Optionally and preferably deflecting apparatus 110 is disposed along a radial cross-section of flow tube 102.

Optionally flow tube 102 may be made of optional materials adept for medical use for and are biocompatible materials. Optionally and preferably flow tube 102 may for example be provided from polymers, super-elastic polymers, memory shaped polymers, hybrid polymers, or the like as is known in the art.

Now referring to FIG. 2-3 depicting a schematic illustration of flow tube 102, flow tube 102 is a substantially cylindrical tube having a substantially open lumen 102L. Flow tube 102 has a length defined between a distal end 102d and a proximal end 102p. The substantially open lumen 102L is configured to allow air to flow from proximal end 102p to distal end 102d. Flow tube 102 has a wall 102w defined between an inner diameter 102i and an outer diameter 102o.

Most preferably flow tube 102 is associated with at least two sensors, preferably a flow sensor 104 and a pressure sensor 106. Optionally and preferably flow sensors 104 and pressure sensor 106 provide data relating to the air pressure and air flow of flowing air depicted by arrows 10 through lumen 102L.

Optionally wall 102w may comprise at least two recesses or dedicated opening provided for receiving flow-meter (104) and a pressure sensor (106).

Flow tube 102 comprises flow deflector apparatus 110 within lumen 102L. Flow deflector 110 provides for deflecting flowing air 10 along the length of tube 102 so as to enable the measurement of air flow and pressure with sensors 104, 106 respectively under variable conditions. Preferably apparatus 110 comprises actuator 112, axle 114, and deflecting leaf/non-occluding shutter 116, as previously described.

Optionally deflecting apparatus 110 may be disposed along the length of tube 102 at a distance 102a defined between proximal end 102p and axle 114. Optionally tube 102 may provide for controlling the location of apparatus 110 by determining and controlling distance 102a.

Optionally flow tube 102 may comprise at least one or more embedded channel (not shown) within wall 102w along the tube's length. Optionally such embedded channel may facilitate for wiring and electronically coupling portion of deflection apparatus 110, flow-meter sensor 104, and/or pressure sensor 106 for coupling with processing module 50.

Optionally apparatus 110 may be disposed within two parallel totally embedded channel (not shown) disposed within wall 102w along the length of tube 102. Optionally such totally embedded channels may facilitate placing apparatus 110 at a controllable distance 102a within lumen 102L.

Optionally axle 114 comprises a first end 114a disposed within wall 102w and a second end 114b extending through flow tube wall 102w, to associate with axle adaptor 112 that is in turn provided for coupling and/or associating with actuator 108. Optionally second end 114b may be adapted for associating with an actuator/driver (108) directly without adaptor 112.

Preferably axle 114 is provided to drive non-occluding shutter leaf 116 within flow tube lumen (102L) in at least one direction, for example as in the rotational axis depicted by arrow 118r or in the vertical axis depicted by arrow 118v.

Axle 114 is associated with a deflector leaf member 116 provided for deflecting airflow within the lumen of flow tube 102, wherein leaf 116 is characterized in that leaf 116 is configured not to occlude airflow through flow-tube lumen 102L therein to maintaining normal breathing physiology when a user breaths through flow-tube 102, according to the present invention. Preferably leaf 116 may be controllably manipulated with axle 114 to assume at least two positions within said flow tube lumen 102L, a first leaf position provided to maintain said flow-tube lumen substantially open, leading to non-deflected airflow 10, depicted in FIG. 2A-B, and a second leaf position provided to deflect airflow through said flow tube, depicted in FIG. 3A-B, leading to deflected air flow 12.

Optionally deflecting leaf 116 that is characterized in that it is configured not to occlude airflow through flow-tube lumen 102L and therein to maintaining normal breathing physiology, is further configured to be a substantially flat leaf having a substantially circular profile configured to having a diameter that is to be up to about 50% of said flow tube diameter. Optionally leaf 116 may be configured to deflect airflow 10, 12 within flow-tube lumen 102L wherein the surface area of leaf 116 configured to be substantially equivalent to up to about 50% the cross-sectional area the flow-tube.

FIG. 2A shows a cross section view of tube 102 along its length, showing leaf 116 in its small profile configuration that substantially allows for un-deflected airflow 10 to flow from proximal end 102p to distal end 102d. FIG. 2B shows a radial cross section view of tube 102, viewed from the proximal end 102p toward distal end 102d, showing that leaf 116 assumes a non-deflection configuration.

FIG. 3A shows a cross section view of tube 102 along its length, showing leaf 116 in its expanded profile configuration that substantially deflect airflow 12 to flow from proximal end 102p to distal end 102d, around leaf 116, while maintaining normal breathing physiology for the user (patient). FIG. 3B shows the radial cross section view of tube 102, viewed from the proximal end 102p toward distal end 102d, showing the leaf 116 assumes the expanded profile that deflects airflow through tube 102. Leaf 116 is configured not to takes up no more than 50% of the cross-sectional surface area of tube lumen 102L, therein deflected airflow 12 through the tube while allowing normal breathing physiology even when leaf 116 is in the expanded configuration.

Optionally the leaf 116 may switch between configurations at a given rate. Optionally the leaf 116 switches positions at a frequency from about 2 Hz up to about 10 Hz. Optionally the leaf 116 switches positions at a frequency of up to about 15 Hz. Optionally the leaf 116 switches positions at a frequency from about 1 Hz. Optionally leaf 116 may be switched between configurations according to physician determined intervals. Optionally leaf 116 may be switched between configurations according to randomly determined intervals. Optionally leaf 116 may be manually switched between configuration by a care giver, physician, nurse, trained individual, and/or a patient. Optionally leaf 116 may switch positions by remote control provided by module 50. Optionally leaf 116 may switch position according to a testing protocol that is individualized. Optionally leaf 116 may switch position according to a testing protocol that is determined based on a treatment protocol, the type of anomaly that is checked, disease state, the like or any combination thereof.

Most preferably the variation both in airflow and air pressure as measured with sensors 104 and 106 while the non-occluding leaf 116 is disposed in the low profile configuration (FIG. 2A-B) and the expanded configuration (FIG. 3A-B) is gathered by module 50 and for analysis. Optionally and preferably the resultant graphical representation of the changes in flow and pressure may be displayed to a user, printout, saved to a computer readable media, communicated to a higher processing center, communicated to a server, any combination thereof or the like.

FIG. 4A-D show graphical depiction of the measured parameters provided with flow tube 102 according to optional embodiments of the present invention.

Figure 4A:
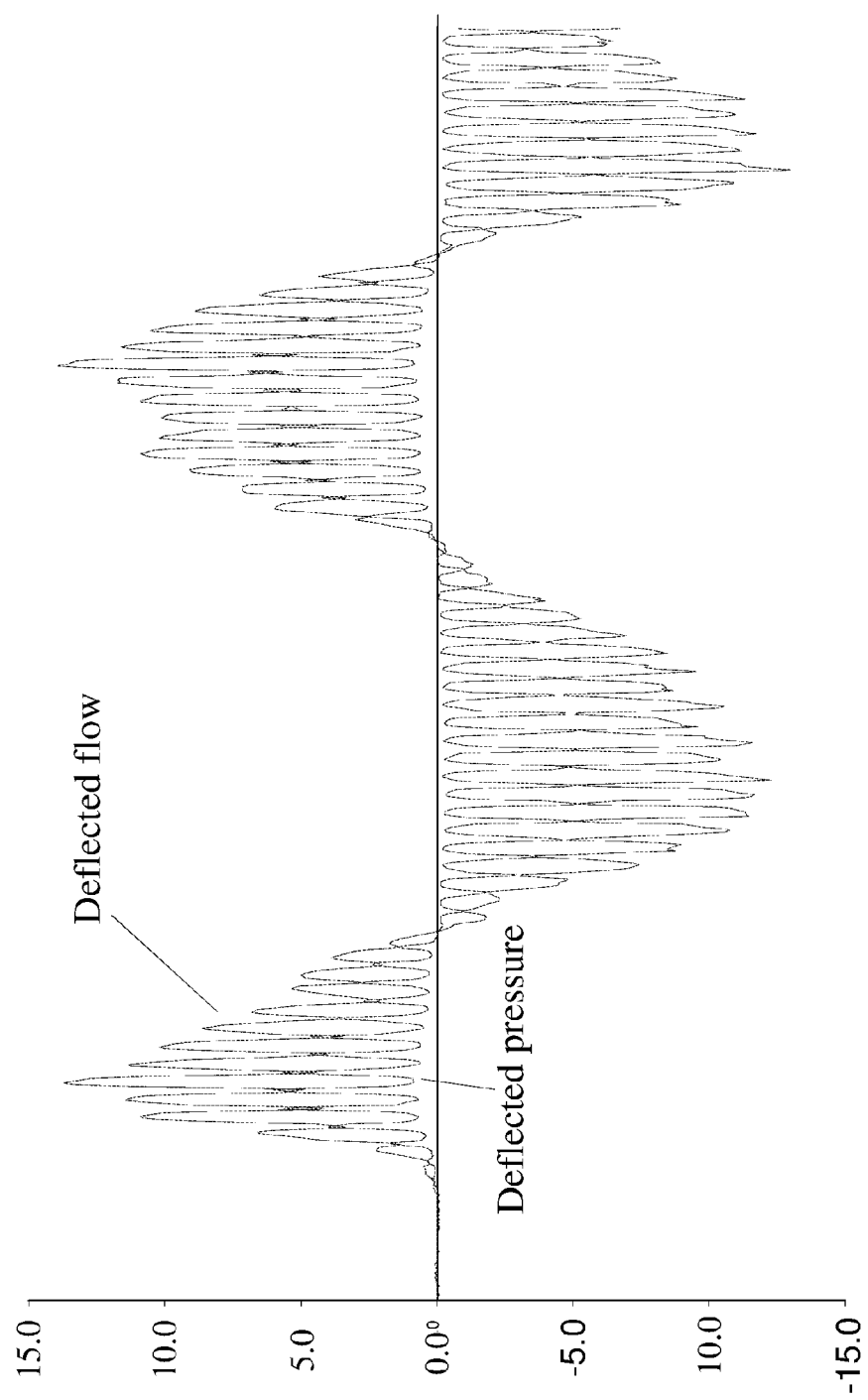
FIG. 4A-D show graphical depiction of the measured parameters according to optional embodiments of the present invention.
Figure 4B:
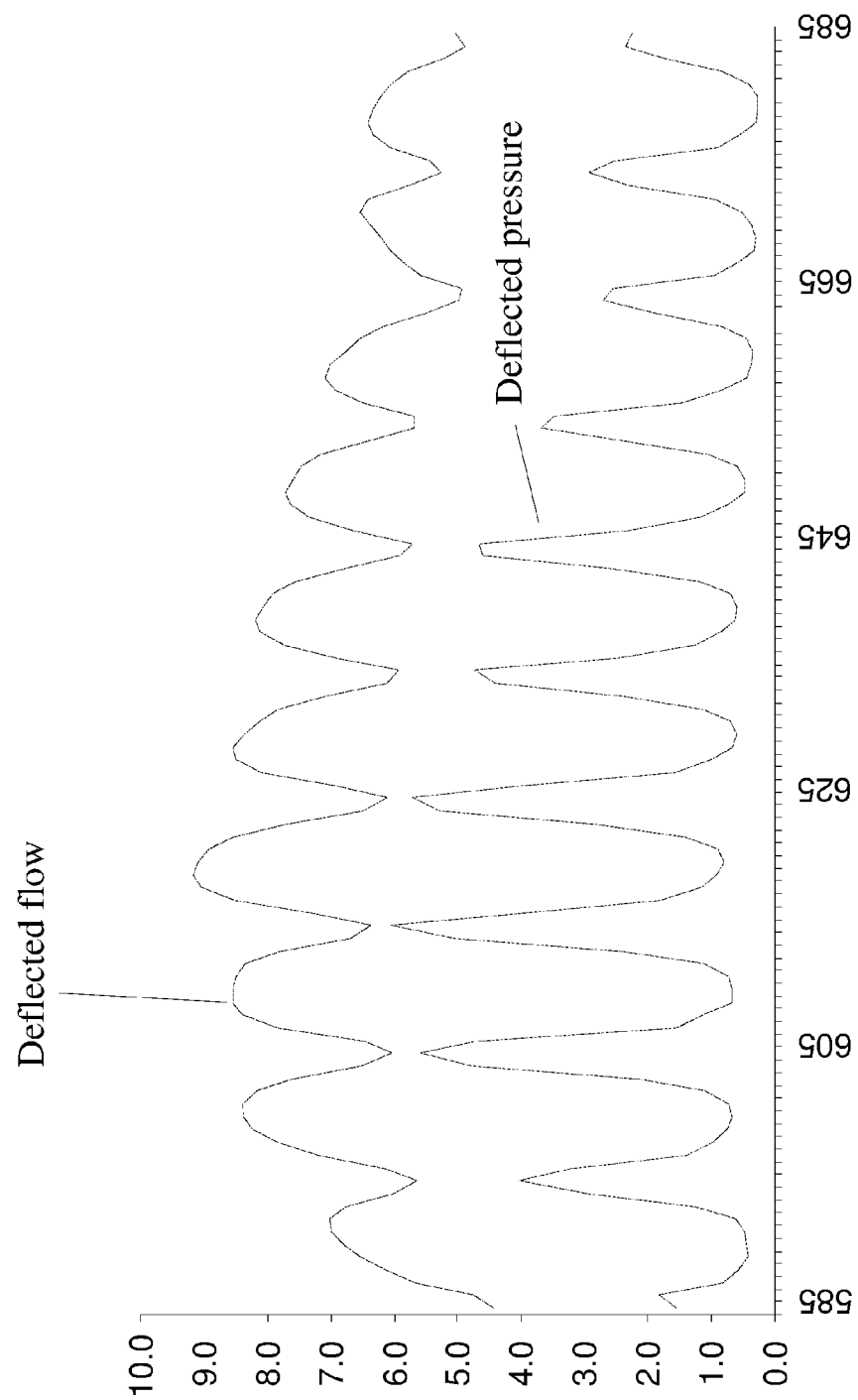
Figure 4C:
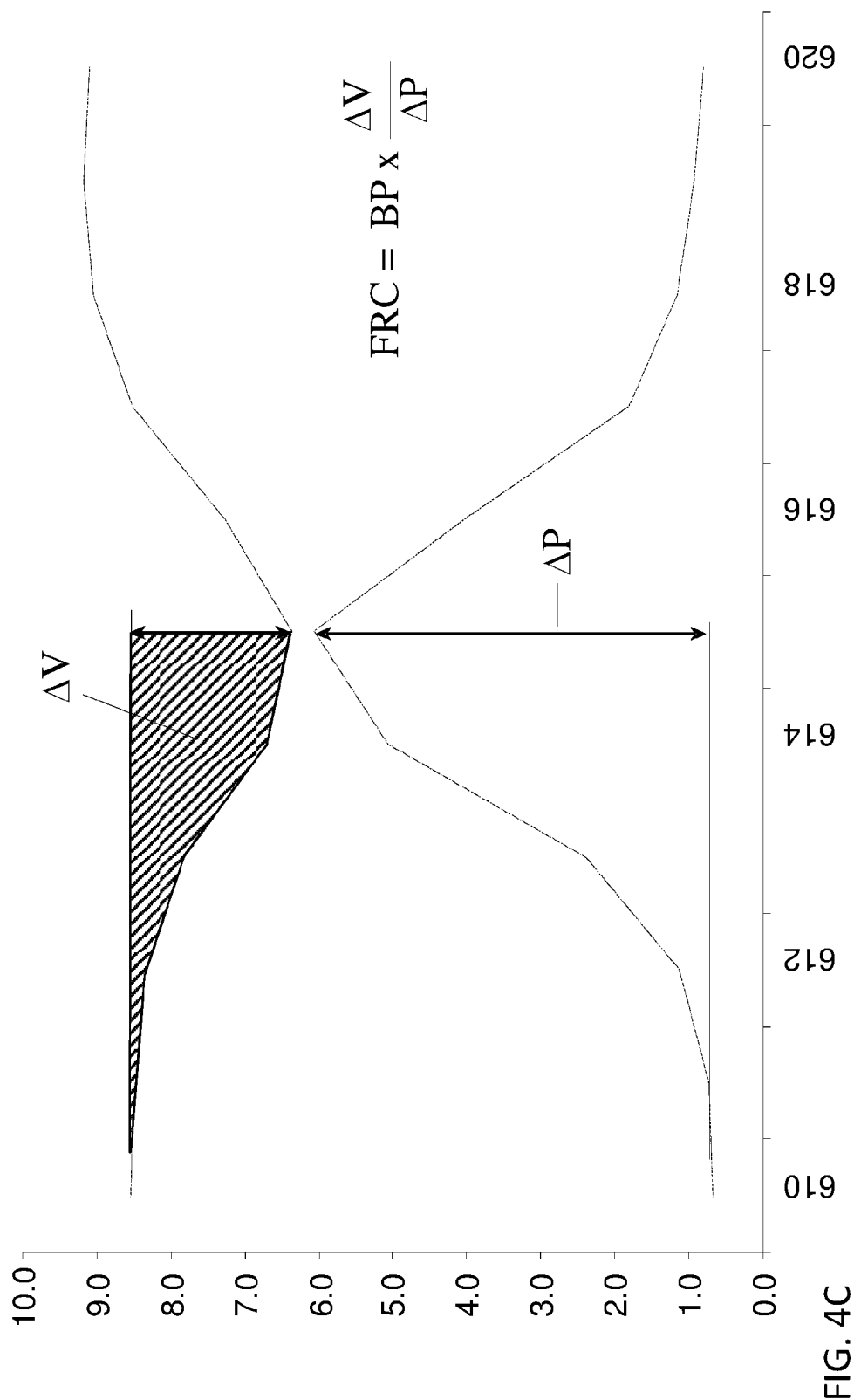

FIG. 4A shows the continuous graphical representation that shows the overall behavior of the changes in air flow and pressure provided with tube 102. The upper trace shows the fluctuations in deflected airflow through tube 102 while leaf 116 assumed different profiles. The lower trace shows the fluctuations in deflected air pressure through tube 102 while leaf assumed different portfolios. FIG. 4B shows a close up of the traces shown in FIG. 4A where the traces for changing airflow, upper trace, and changing pressure, lower trace, are more readily visible. FIG. 4C shows a close up of the traces shown in FIG. 4B where the traces for changing airflow, upper trace, and changing pressure, lower trace, are more readily visible.

FIG. 4A-C show a sinusoidal trace depicting the fluctuations in air flow and air pressure through the flow tube under different configurations of non-occluding leaf 116. The sinusoidal trace provides for determining the changes in volume ($\Delta V$, as shown in the shaded area), and changes in pressure ($\Delta P$) by determining the area below the curve, between peak and tough, for example as shown in FIG. 4C. The area underneath the curve is then utilized in to solve the FRC equation:

$$FRC = BP * \frac{\Delta V}{\Delta P}$$

Where FRC is the Functional Residual Capacity and BP is the base barometric pressure (atmospheric pressure).

Figure 4D:
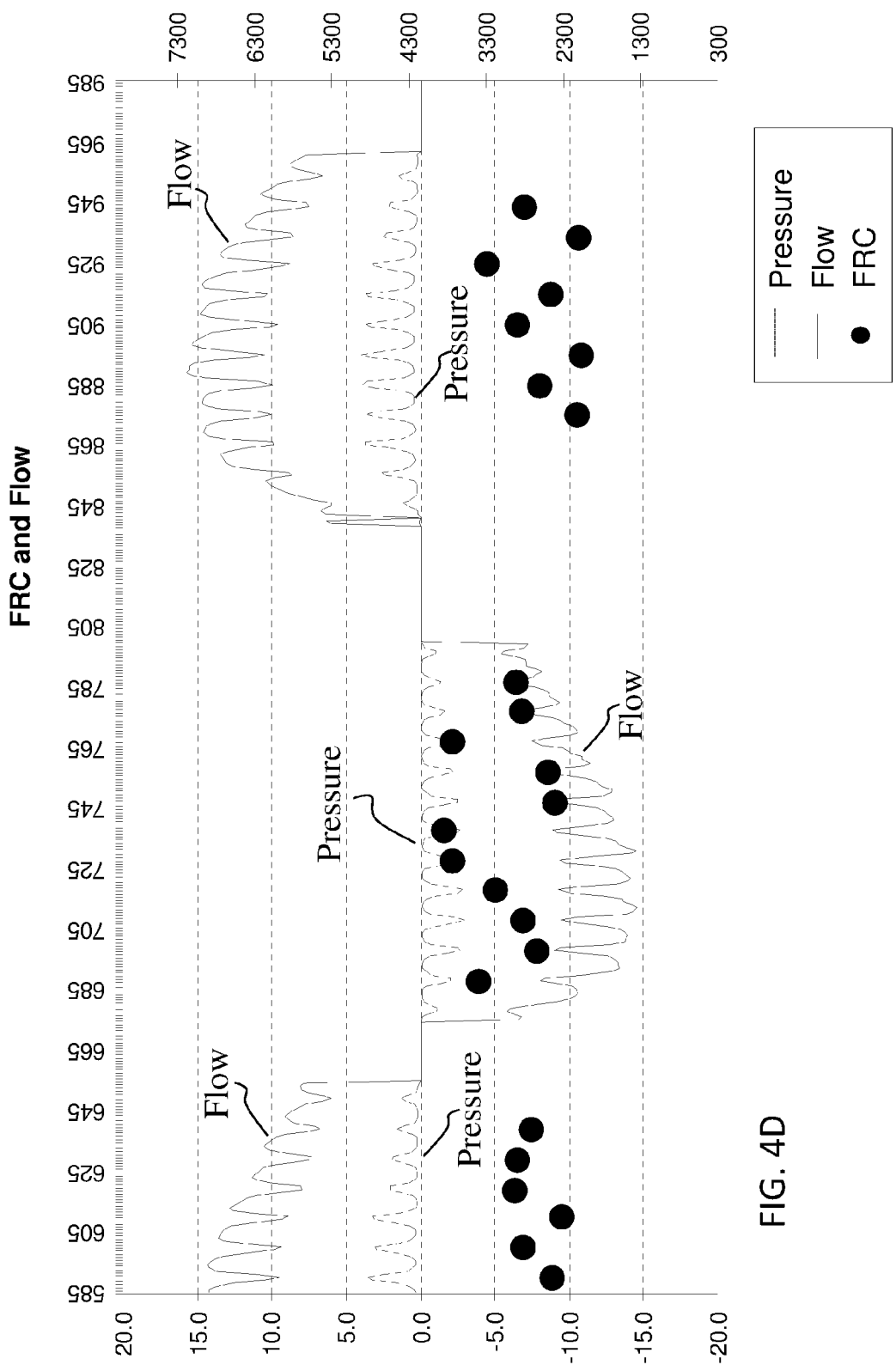

The resultant FRC may be displayed in graphical form for example as shown in FIG. 4D. Once FRC is determined other lung volume parameters may be inferred, as is known in the art.

Figure 5:
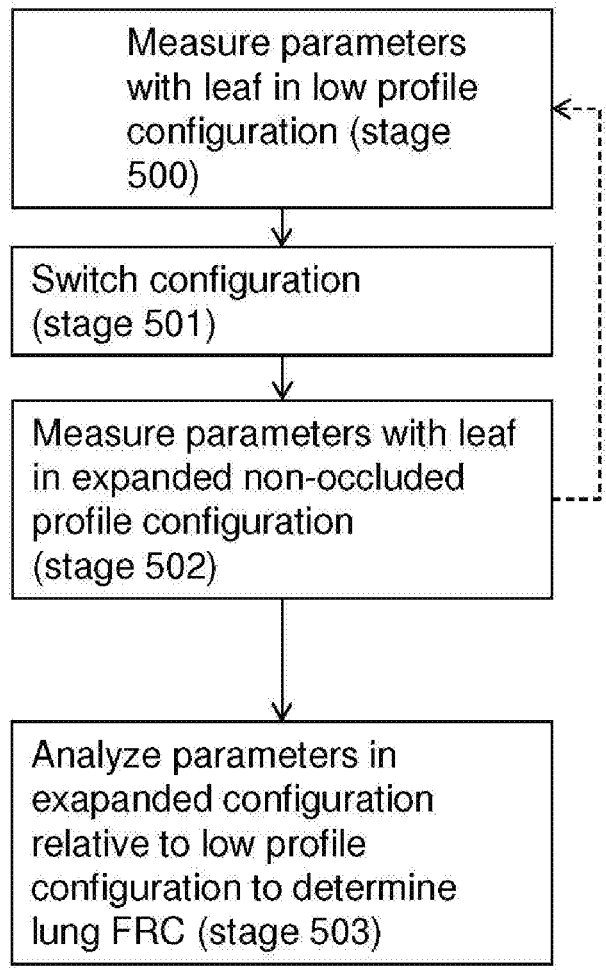
FIG. 5 shows a flowchart of a method according to an optional embodiment of the present invention.

FIG. 5 shows a flowchart depicting the method for determining FRC with the spirometer 100 of the present invention comprising a non-occluding spirometer leaf shutter 116. First in stage 500 a patient is breaths through flow tube 102 when leaf 116 is in the low profile configuration, allowing air flow through tube 102 as depicted by un-deflected airflow 10. Module 50 is preferably utilized to store data sensed with sensors 104, 106. Next, following in stage 501, leaf 116 configuration is changed from low profile, FIG. 2A-B, to expanded profile, FIG. 3A-B, optionally by utilizing actuator 112 to rotate axle 114 along radial axis 118r with lumen 102L. Next in stage 502, flow tube 102 now having a deflected air flow 12, with the expanded configuration of leaf 116 deployed within lumen 102L, allows sensors 104, 106 to sense while preferably module 50 monitors the changes.

Optionally following stage 502, the flow tube 102 may be revert to stages 500 and continue the detection process until the end of the measuring protocol.

Preferably once all measurements have been recorded and all necessary stages performed according to the required protocol, in stage 503 the previously recorded data is analyzed with module 50 to determine the lung FRC.

Optionally once lung FRC is determined by module 50, the results may be displayed, communicated and/or provided as an output to a user or a computer for further processing. For example, the results may be communicated via communication channels 52 to a health care professional, to a user, to an Emergency call center, or the like. Optionally the results may be communicated to trigger an alarm state when compared to threshold levels.

Optionally and preferably the processing and communication module 50 provides for controlling the timing of stages 500-503.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

While the invention has been described with respect to a limited number of embodiments, it will be appreciated that many variations, modifications and other applications of the invention may be made.

What is claimed is:

1. A flow tube apparatus provided for determining the lung Functional Residual Capacity (FRC), the apparatus comprising:
   a) a flow tube having a length defined between a distal end and a proximal end, having a substantially open lumen configured to allow air to flow from said proximal end to said distal end; said flow tube having a wall defined between an inner diameter and an outer diameter, wherein said inner diameter has at least one of the following profiles along the length of said open lumen: decreasing diameter, increasing diameter, hourglass profile, and wave like profile;
   b) a flow-meter positioned in a first recess disposed within said wall and a pressure sensor positioned in a second recess disposed within said wall;
   c) said flow tube configured to associate with a flow deflecting apparatus comprising:
      i) an axle disposed across the diameter of said lumen at a distance from said proximal end, said axle having a first end disposed within said flow tube wall and a second end extending through and transcending said flow tube wall, wherein said second end is adapted for associating with a deflector driver disposed externally to said flow tube;
      ii) wherein said deflector driver is adapted to drive said axle within said flow tube lumen in at least one direction;
      iii) said axle associated with a deflector leaf member provided for deflecting airflow within said flow tube characterized in that said leaf is configured not to occlude airflow through said flow-tube and therein allow flow through said tube so as to maintain normal breathing physiology along said flow-tube; and wherein said deflector leaf member may be controllably manipulated about said axle to assume at least two non-occluding positions within said flow tube, a first leaf position provided to maintain said flow-tube lumen substantially open and a second leaf position provided to deflect airflow through said flow tube; wherein said axle is adapted to allow both rotational and vertical movement of said leaf within said lumen.

2. The apparatus of claim 1, wherein said deflecting leaf member is configured to be a substantially flat leaf having a substantially circular profile configured to having a diameter that does not exceed 50% of said flow tube diameter.

3. The apparatus of claim 1, wherein said deflecting leaf member is configured to deflect the airflow within said flow-tube wherein the surface area of said leaf does not exceed 50% of the cross-sectional area said flow-tube.

4. The apparatus of claim 1, wherein said deflecting leaf member is configured with a flat geometric shape selected from the group consisting of: ellipsoid, elliptical, circular, ovoid, ring, discoid, polyhedral having n sides where n is at least 3, trapezoid, quadrilateral, square and triangle.

5. The flow tube of claim 1, wherein said wall comprises at least one embedded channel along the length of said tube wall.

6. The flow tube of claim 5, wherein said embedded channel facilitates for associating said flow-meter, said pressure sensor and, said flow deflecting apparatus with a processing device.

7. The flow tube of claim 1, further comprising at least one or more auxiliary flow deflecting apparatus.

8. The apparatus of claim 1, wherein said driver drives said deflecting leaf member in at least one axis about said axle within said lumen selected from a rotational axis and a vertical axis.

9. The apparatus of claim 1, wherein said deflector apparatus is provided to rotate said deflecting leaf member at a frequency of up to about 15 Hz.

10. The apparatus of claim 1 provided from multi-use material that may be sterilized or from disposable single use material.

11. The apparatus of claim 1, wherein said flow meter and said pressure sensor are embedded within said flow tube wall.

12. The apparatus of claim 1, wherein said deflecting leaf member is configured to assume at least two or more profile shape configurations, said deflecting leaf member is provided from at least one of the following: shape memory material, super elastic material, super elastic polymer, super elastic alloy and super elastic plastic.

13. The device of claim 1, wherein said flow-tube is associated with a processing module configured to process data received from said flow-meter, pressure sensor, and said flow deflecting apparatus.

\* \* \* \* \*